(12) United States Patent
Ali

(10) Patent No.: US 6,248,591 B1
(45) Date of Patent: Jun. 19, 2001

(54) METHOD FOR IN VITRO EVALUATION OF SAFETY OF INJECTABLE HERBAL EXTRACTS

(76) Inventor: Majid Ali, 8 Alcott St., Teaneck, NJ (US) 07666

( * ) Notice: Subject to any disclaimer, the term of this patent is extended or adjusted under 35 U.S.C. 154(b) by 0 days.

(21) Appl. No.: 09/386,977

(22) Filed: Aug. 31, 1999

(51) Int. Cl.⁷ .................................................. G01N 33/48

(52) U.S. Cl. ................................ 436/63; 436/164; 435/4; 435/29

(58) Field of Search .............................. 436/63, 69, 164; 435/2, 4, 29

(56) References Cited

PUBLICATIONS

Majid Ali, "The Use of High–Resolution Microscopy for In Vitro Evaluation of Safety of Injectable Herbal Extracts," J. Integrative Medicine 2:70–72 (1998).

*Primary Examiner*—Maureen M. Wallenhorst
(74) *Attorney, Agent, or Firm*—Ostrolenk, Faber, Gerb & Soffen, LLP

(57) ABSTRACT

A method of evaluating the safety of a herbal extract for parenteral use is described which consists of contacting blood cells with the extract and examining the blood cells for at least one membrane deformity. In addition, another method of evaluating the safety of a herbal extract for parenteral use is also described which consists of contacting plasma with the extract and examining the plasma for formation of a condition such as zones of congealing, microclots and microplaques.

16 Claims, No Drawings

METHOD FOR IN VITRO EVALUATION OF SAFETY OF INJECTABLE HERBAL EXTRACTS

FIELD OF THE INVENTION

The present invention relates to in vitro methods for evaluating the safety of whole herb extracts for parenteral use by examination of blood cells and plasma after exposing them to various concentrations of extracts with high-resolution phase-contrast microscopy.

BACKGROUND OF THE INVENTION

A large number of pharmacologic agents are derived from plant sources. The traditional approach to preparation of such pharmaceutical agents employs fractionation of natural, plant-derived substances into their individual bio-active components followed by chemical characterization of one or more fractions for use as single drugs. While this approach has yielded a rich formulary of potent drugs for managing acute disorders, the long-term effects of such drugs carry significant potential for adverse effects. The use of whole herb extracts, by contrast, are generally not as potent as plant-derived drugs. This has been validated by empirical observations with combinations of herbs formulated to restore altered bowel, blood, liver, and other body organ ecosystems (A. Majid, J. Integrative Medicine 2:4–55, 1988; A. Majid, "The Cortical Monkey and Healing", pp. The Institute of Preventive Medicine, Bloomfield, N.J. 1989; A. Majid, "The Cortical Monkey and Healing", pp. 73–75, Institute of Preventive Medicine, Bloomfield, N.J. 1990; and A. Majid, "Healing, Miracles and the Bite of the Gray Dog", Life Span, Denville, N.J. 1997). It seems likely that such safety follows use of a large number of herbs in smaller amounts. Beyond that, there is the important issue of plant substances carrying their own "counteracting" components that neutralize some of the toxicity of individual and highly concentrated fractions such as those used in plant-derived drugs. Thus, highly purified plant fractions (drugs), while effective in acute illnesses, may not be optimal for use for slow and sustained reparative work for damaged body organ ecosystems.

Herbs have been used for medicinal uses by the oral route for hundreds of years (Theophrastus (370–285 BC), "Enquiry into Plants", in 2 vols., translated by A. Hort, W. Heinmann, London, 1916; "Herbs, Spices, and Medicinal Plants: Recent Advances in Botany, Horticulture, and Pharmacology", Lyle E. Cracker and James E. Sinom, eds, Oryx Press, Phoenix, Ariz., Vol. 1, 1986; "Folk Medicine: The Art and the Science", Richard P. Steiner, Ed., American Chemical Society, Washington, D.C., 1986, ISBN-0-8412-0939-1; J. A. Duke, "CRC Handbook for Medicinal Herbs", CRC Press, Boca Raton, Fla. 1985). Injectable extracts of individual compounds derived from plant sources, such as colchicine, have been used for their medicinal values for decades in many countries. The Chinese have clinically used extracts of whole herbs with increasing frequency during the last few decades. It is known that certain herbs, when administered intramuscularly, produce results that contrast with those empirically observed with oral use (J. A. Duke, "The Green Pharmacy", Rodale Press, Emmanus, Pa. 1997, ISBN-0-87596-316-1). One possible explanation for that phenomenon may be that active ingredients of such herbs undergo conformational changes when they are subjected to the normal digestive/absorptive processes after oral administration.

The potential clinical benefits of parenteral use of mixtures of whole herb extracts need to be explored for several reasons. First, extensive empirical experience indicates that injectable forms of many therapeutic agents are far more effective than the preparations for oral use. Empirical experience with mixture of injectable herb extracts, though limited, suggests the possibility that the clinical outcome with the use of injectable extracts may be improved. Second, there is the potential of injectable herbal mixtures providing greater benefits just as oral herbal mixtures give superior results than the use of single herbs. Third, there are many anecdotal reports of control of malignant neoplasms and other serious autoimmune disorders with injectable herbal mixtures for which there are no effective drug therapies. However, details of such therapies are rarely published, and the safety of their use cannot be assumed.

The clinical safety of herbs, in general, has been established by empirical use by herbologists and integrative physicians. A central issue in parenteral use of herbal formulations, however, is the potential danger of serious hemolytic and nonhemolytic reactions when they are given parenterally. Specifically, there is the issue of phytoagglutinins, natural plant-derived substances with ability to bind a large variety of cell membrane ligands, causing serious hemolytic and nonhemolytic reactions (D. L. J. Freed, "Dietary Lectins and disease", In: Food Allergy and Intolerance, J. Brostoff and S. J. Challacombe, Eds., 1987, Bailliere Tindal, East Sussex, England; P. Ganguly et al., Biochim. Biophys. Acta 627:256–261, 1980; I. hilgert et al., Nature 284:273–275, 1980). An example of a highly toxic phytoagglutinin is that derived from beans of the castor plant. Even commonly ingested wheat germ agglutinins are known to cause agglutinin reactions in certain individuals (D. L. J. Freed, "Dietary Lectins and disease", In: Food Allergy and Intolerance, J. Brostoff and S. J. Challacombe, Eds., 1987, Bailliere Tindal, East Sussex, England). Accordingly, there is a need for evaluating the safety of whole herb extracts for parenteral use.

SUMMARY OF THE INVENTION

It is, therefore an object of the invention to provide an vitro method for evaluating the safety of whole herbal extracts.

In one embodiment, the present invention provides a method of evaluating the safety of a herbal extract for parenteral use comprising: (a) contacting blood cells with the extract; and (b) examining the blood cells for at least one membrane deformity.

In another embodiment the present invention provides a method of evaluating the safety of a herbal extract for parenteral use comprising: (a) contacting plasma with the extract; and (b) examining the plasma for formation of a condition selected from the group consisting of zones of congealing, microclots and microplaques.

Other objects and advantages of the present invention will become apparent from the following description and appended claims.

DETAILED DESCRIPTION OF THE INVENTION

It has now been found that the objectives of this invention are realized by employing in vitro microscopic methods for direct assessment of the immediate and delayed effects of contacting blood cells and plasma components with whole herb extracts. The blood cells are examined for membrane deformities. Preferably, the blood cells examined are erythrocytes. Also preferably, the membrane deformity is selected from the group consisting of loss of normal plasticity, wrinkling, and agglutination. When the plasma is contacted with the herbal extract, it is examined for formation of a condition selected from the group consisting of zones of congealing, microclots and microplaques.

While these morphological changes in the cells can occur after exposure to any concentration of herbal extract, the majority of these changes (75% or more, preferably 90% and more preferably 95%) are reversible after a period of time ranging from 15 minutes to one hour. In this case, these concentrations are safe for parenteral use. On the other hand, if these morphological changes are permanent, then the blood cells with the morphological changes are presumed to be senescent or unhealthy as previously described (J. Integrative Medicine, 2:4–55, 1998). Accordingly, adverse side effects would be expected to be associated with parenteral administration of the concentration of herbal extract that causes the significant permanent morphological changes in blood cells and/or plasma.

In practicing the methods of the present invention, it is preferred to contact the blood cells or the plasma with different dilutions of the herbal extract in order to determine the safe concentration of the extract when administered parenterally. The effects of the herbal extracts on blood cells and plasma are examined using microscopy, preferably phase-contrast or darkfield microscopy.

The methods of the present invention provide an early warning of the potential hemolytic reactions caused by parenterally herbal extracts. Thus, an in vitro microscopic method focusing on the effects of injectable herbal extracts can provide valuable information on some immediate and delayed "net" adverse effects on blood cellular and plasma components, and so can be of considerable value. These methods not only allow easy and early detection of herbal extracts that may cause hemolysis (by their hemagglutinins or other components), they also permit selection of the optimal dilutions of extracts that may be safe for parenteral use.

The extraction processes used to make the herbal extracts of the invention utilizes traditional techniques in the art. The extraction is typically carried out at a temperature below that which adversely affects the properties of the extracted herbal composition or is above a reasonable reflux temperature for the extraction solvent of choice, and above that at which meaningful extraction does not occur. Generally, such temperatures range from as low as about 0° C. to 300° C., though temperatures that are higher or lower are feasible. Normally, the temperature of the extraction is dependent upon the boiling or freezing characteristic of the extraction solvent or solution. Moderate temperatures are preferred so long as extraction efficiencies for economic extraction rates are met. As a rule, higher temperatures are reflected in higher extraction rates.

The choice of extraction solvent is typically dependent upon the chemical nature of the herbal component undergoing extraction, the toxicity characteristics of the solvent, boiling and freezing points of the solvent, and the like considerations. Alcohols, such as ethanol, etc., are quite suitable as extraction solvents. Phosphate buffered saline, acetone, diethylether and aqueous ammonia are useful solvents in select cases.

The morphologic observations associated with blood cells and plasma can be made using a microscope, preferably a high-resolution microscope fitted with bright-light, phase contrast and/or darkfield optics. This type of microscope permits direct morphologic study of freshly prepared peripheral blood smears without any staining with a high magnification (15,000×) and good resolution. As described previously (J. Integrative Medicine, 2:4–55, 1998), such microscopy yields detailed information about the morphologic changes occurring in the circulating blood and involving plasma components (such as plasma congealing and microclot formation) as well as blood corpuscles. Specifically, it is possible to study the structure and dynamics of the cell membranes of erythrocytes, lymphocytes and polymorphonuclear cells. Also, direct observations of the morphology and movements of intracellular granules permit evaluation of functional integrity of some types of leukocytes. Darkfield optics can used to distinguish between highly retractile blood platelets and non-refractile platelet-like bodies in the blood smears. Phase-contrast optics are also used for the study of plasma alterations such as plasma congealing, and microclot and microplaque formation.

EXAMPLE 1

The injectable extracts of six herbs were prepared by extraction of active ingredients with phosphate-buffered saline followed by ultracentrifugation and ultrafiltration as described elsewhere (A. Majid et al., J. Integrative Medicine, 1998 (The Journal of Investigative Medicine, 3:112–119, 1999). Briefly, The ingredients of the herbs were excretacted in phosphate-buffered saline at physiological pH (7.6). The particulate materials were removed by high speed untracentrifugation. The extracts were sterilized by ultrafiltration (0.2 micron filter).

The following herbs were included in this study: *Hydratis canadensis* (goldenseal root), *Foeniculum vulgare* (fennel seeds), *Hypericum perforatum* (St. John's wort), Glycyrrhiza (licorice root), *Rubus villosus* (blackberry root), and *Herba impatiens pallidar.*

For evaluating the immediate and delayed effects of various concentrations of the herbal extracts on the plasma components and blood corpuscles, a drop of 1:10, 1:100, 1:500, 1:1,000, 1:5,000, 1:10,000, and 1:100,000 dilutions of each herbal extracts was added to the freshly prepared smears, followed by gentle mixing of the extract with blood elements. The smears were then covered with a coverslip and examined with phase-contrast microscopy.

All extracts tested in 1:10 dilutions caused diffuse erythrocyte agglutination and other forms of membrane damage. Strong concentrations (1:10 to 1:100 of all extracts caused a variety of erythrocyte membrane deformities, including loss of normal plasticity, wrinkling, spiking, and agglutination. Some cells were lysed. With increasing dilutions, such changes were observed with decreasing frequency. Still, some evidence of erythrocyte membrane damage was seen with all herbal extracts in dilutions less than 1:1,000 when smears were examined immediately. However, in most cases, such changes resolved spontaneously within 30 to 60 minutes, indicating reversibility of such membrane changes involving most cells with weaker dilutions. A small number of erythrocytes in most smears did not recover, and a few underwent lysis.

The plasma changes accompanying the above described cellular changes included formation of zones of congealing, microclots, and microplaques. With the use of different dilutions of herbal extracts, it was possible to select dilutions of herbal extracts that caused limited and spontaneously resolving patterns of damage to blood cells or plasma. Intramuscular injections of ultrafiltered herbal extracts in those dilutions to four volunteers, after obtaining appropriate consents, did not cause any immediate or delayed adverse local and systemic effects.

EXAMPLE 2

Table 1 shows results of dilution studies as described in Example 1 performed to investigate reversibility of erythrocyte membrane changes induced by exposure to herbal extracts. All extracts used were in 1:20 w/v strengths. Peripheral smears were examined immediately and 30 minutes after the addition of one drop of the herbal extract dilutions shown.

TABLE 1

Effect of Extract Dilution on
Reversibility of Erythrocyte Membrane Damage

| Herb | Dilution | Reversibility Score |
|---|---|---|
| *Radix Hydrastis canadensis* | 1:5,000 | >98% |
| *Hypericum perforatum* | 1:1,000 | >95% |
| *Semen Foeniculum vulgare* | 1:1,000 | >98% |
| *Radix Glycyrrhiza glabra* | 1:1,000 | >95% |
| *Radix Rubus fruticosus* | 1:5,000 | >95% |
| *Herba Impatiens pallidar* | 1:5,000 | >95% |

The results in table 1 indicate the dilutions of the herbal extracts that are safe to administer parenterally since at least 95% of the erythrocyte membrane changes induced by exposure to these dilutions of herbal extracts are reversible.

The invention has been described in terms of preferred embodiments thereof, but is more broadly applicable as will be understood by those skilled in the art. The scope of the invention is therefore limited only by the following claims.

What is claimed is:

1. A method of evaluating the safety of a herbal extract for parenteral use comprising:
   (a) contacting blood cells with the extract; and
   (b) examining the blood cells for at least one membrane deformity.

2. The method of claim 1, wherein the blood cells are erythrocytes.

3. The method of claim 1, wherein the membrane deformity is selected from the group consisting of loss of normal plasticity, wrinkling, and agglutination.

4. The method of claim 1, wherein the blood cells are contacted with different dilutions of the herbal extract.

5. The method of claim 1, wherein the herbal extract is obtained by extracting a herb in phosphate buffered saline followed by ultracentrifugation and ultrafiltration.

6. The method of claim 1, wherein the herbal extract is extracted from a herb selected from the group consisting of *Hydrastis canadensis, Foeniculum vulgare, Hypericum perforatum,* Glycyrrhiza, *Rubus villosus,* and *Herba impatiens pallidar.*

7. The method of claim 1, wherein microscopy is used to examine the blood cells.

8. The method of claim 7, wherein the microscopy is phase-contrast microscopy.

9. The method of claim 7, wherein the microscopy is darkfield microscopy.

10. A method of evaluating the safety of a herbal extract for parenteral use comprising:
    (a) contacting plasma with the extract; and
    (b) examining the plasma for formation of a condition selected from the group consisting of zones of congealing, microclots and microplaques.

11. The method of claim 10, wherein the plasma is contacted with different dilutions of the herbal extract.

12. The method of claim 10, wherein the herbal extract is obtained by extracting a herb in phosphate buffered saline followed by ultracentrifugation and ultrafiltration.

13. The method of claim 10, wherein the herbal extract is extracted from a herb selected from the group consisting of *Hydrastis canadensis, Foeniculum vulgare, Hypericum perforatum,* Glycyrrhiza, *Rubus villosus,* and *Herba impatiens pallidar.*

14. The method of claim 10, wherein microscopy is used to examine the plasma.

15. The method of claim 14, wherein the microscopy is phase-contrast microscopy.

16. The method of claim 14, wherein the microscopy is darkfield microscopy.

* * * * *